United States Patent [19]

Hill et al.

[11] Patent Number: 4,645,756

[45] Date of Patent: Feb. 24, 1987

[54] [α,ω-BIS(DIPHENYLPHOSPHINO)HY-DROCARBON]BIS[(THIOSUGAR)GOLD] AND BIS[(SELENOSUGAR)GOLD] DERIVATIVES, PHARMACEUTICAL COMPOSITIONS AND METHOD OF USE

[75] Inventors: David T. Hill, North Wales; Randall K. Johnson, Ardmore, both of Pa.

[73] Assignee: Smith Kline Beckman Corporation, Philadelphia, Pa.

[21] Appl. No.: 781,438

[22] Filed: Sep. 27, 1985

[51] Int. Cl.$^4$ .......................... A61K 31/70; C07H 5/10
[52] U.S. Cl. ..................................... 514/24; 536/17.1; 536/122
[58] Field of Search ................. 514/24; 536/17.1, 122; 556/14

[56] References Cited

U.S. PATENT DOCUMENTS

| | | | |
|---|---|---|---|
| 3,708,579 | 1/1973 | McGusty et al. | 514/24 |
| 4,096,247 | 6/1978 | Lantos | 514/24 |
| 4,096,249 | 6/1978 | Lantos | 514/24 |
| 4,096,250 | 6/1978 | Hill | 514/24 |
| 4,201,775 | 5/1980 | Filan et al. | 536/17.1 |

FOREIGN PATENT DOCUMENTS

WO85/00747 2/1985 PCT Int'l Appl. .

OTHER PUBLICATIONS

Sutton et al., *J. Med. Chem.*, 15(11), 1095-98 (1972).
Mirabelli et al., *Proc. Amer. Assn. Cancer Res.*, 25, 367 (1984).
Simon et al., *Cancer Res.*, 41, 94 (1981).
Mirabelli et al., *Cancer Res.*, 45, 32 (1985).
Struck et al., *J. Med. Chem.* 9, 414-16 (1966).

*Primary Examiner*—Johnnie R. Brown
*Attorney, Agent, or Firm*—Carol G. Canter; Janice E. Williams; Alan D. Lourie

[57]  ABSTRACT

This invention relates to [α,ω-bis(diphenylphosphino)-hydrocarbon]bis[(thiosugar)gold] and bis[(selenosugar)gold] derivatives, pharmaceutical compositions comprising an effective tumor cell growth-inhibiting amount of such a derivative, and a method of treating tumor cells sensitive to such a derivative which comprises administering a tumor cell growth-inhibiting amount of such a derivative to an animal afflicted by said tumor cells.

17 Claims, No Drawings

[α,ω-BIS(DIPHENYLPHOSPHINO)HYDROCARBON]BIS[(THIOSUGAR)GOLD] AND BIS[(SELENOSUGAR)GOLD] DERIVATIVES, PHARMACEUTICAL COMPOSITIONS AND METHOD OF USE

CROSS REFERENCE TO RELATED APPLICATIONS

This application is a continuation-in-part of Ser. No. 693,416, filed Jan. 22, 1985, which is abandoned.

BACKGROUND OF THE INVENTION

This invention relates to novel [bis(diphenylphosphino)alkyl]bis-gold[I] derivatives which have tumor cell growth-inhibiting activity, pharmaceutical compositions containing such novel derivatives, and a method for treating tumor cells sensitive to such derivatives by administering tumor cell growth-inhibiting amounts of such novel derivatives to a host animal afflicted by such tumor cells. Sutton et al., *J. Med. Chem.*, 15 (11), 1095-98 (1972), disclose antiarthritic properties of certain trialkylmonophosphine gold thiosugar complexes. Mirabelli et al., *Proc. Amer. Assn. Cancer Res.*, 25, 367 (1984) disclose that certain monophosphinegold (I) thiosugar complexes, including auranofin and related triethylphosphino gold(I) thiolates, had respectable activity in an intraperitoneal P388 leukemia tumor model. Simon et al., *Cancer Res.*, 41, 94 (1981), and Mirabelli et al., *Cancer Res.*, 45, 32 (1985), disclose that auranofin possesses significant antitumor effects in animals bearing P388 leukemia. Dumas et al., Japanese Patent Application No. 58,192,893, published Nov. 10, 1983, disclose the selenium analog of auranofin and other related triethylphosphino gold(I) selenolates, and report their utility as antiarthritic agents. Struck et al., *J. Med. Chem.*, 9, 414-16 (1966), disclose cytotoxic activity of ethylenebis(diphenylphosphine). None of the aforementioned references disclose or suggest the [bis(diphenylphosphino)alkyl]bis-gold(I) thiosugar or selenosugar derivatives of the instant invention, or that they have tumor cell growth-inhibiting activity.

SUMMARY OF THE INVENTION

This invention relates to diphenylphosphino gold [I] derivatives of the formula:

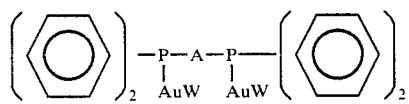

wherein:
A is $(CH_2)_n$ or cis CH=CH;
n is 1 to 6; and
W is the same and is thiosugar or selenosugar.
The attachment of W to the gold atom is through the sulfur atom of the thiosugar or selenium atom of the selenosugar.

This invention also relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of formula (I).

Another aspect of this invention is a method of inhibiting the growth of animal tumor cells sensitive to a compound of formula (I) which comprises administering to an animal afflicted with said tumor cells, an effective, tumor cell growth-inhibiting amount of a compound of formula (I).

DETAILED DESCRIPTION OF THE INVENTION

By the term "thiosugar" is meant any 1-thioaldose. Examples of such thiosugars include 1-thioglucose, 1-thiogalactose, 1-thiomannos, 1-thioribose, 1-thiomaltose, 1-thiofucose, thioribofuranose tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose, tri-O-acetyl-1-thiofucose.

By the term "selenosugar" is meant any non-acetylated 1-selenoaldose. Examples of such selenosugars include 1-selenoglucose, 1-selenomannose, 1-selenogalactose, 1-selenoribose, 1-selenomaltose and 1-selenofucose.

Preferred compounds of formula (I) include those wherein W is 1-thioglucose, 1-thiogalactose and 1-thiomannose. These compounds are preferred because they exhibit particularly active tumor-inhibiting activity in a variety of test systems.

All the compounds encompassed by formula (I) can be prepared by methods available to one skilled in the art. Generally, the compounds of formula (I), wherein W is a non-acetylated 1-thioaldose or 1-selenoaldose, are prepared by reacting the appropriate derivative of formula (II):

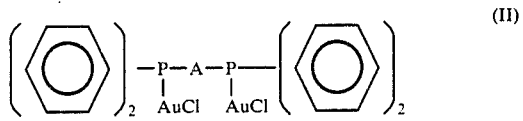

wherein A is as defined above, with the appropriate sodium thiosugar or sodium selenothiosugar. The desired non-acetylated thiosugar or selenosugar can be obtained commercially or by methods available to one skilled in the art.

The desired derivative of formula (II) can be obtained by reacting the appropriate diphosphino hydrocarbon of formula (III):

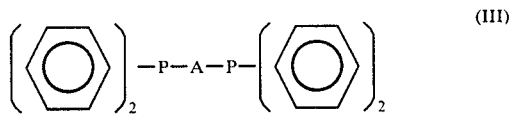

wherein A is as defined above, directly with chloroauric acid hydrate or a reduced form of the acid hydrate obtained by treatment with thiodiglycol. For example, a solution of thiodiglycol in a nonreactive organic solvent, such as methanol or ethanol, is reacted with an aqueous solution of chloroauric acid hydrate cooled to a temperature of from −10° to 0° C., and then treated with a solution of the appropriate formula (III) compound in a nonreactive organic solvent system, such as a mixture of chloroform and methanol, for from one to two hours to give the corresponding formula (II) compound. Similarly, chloroauric acid hydrate in a nonreactive organic solvent, such as methanol or ethanol, is reacted with a solution of the appropriate formula (III) compound at ambient temperature for from one to two hours to give the corresponding formula (II) compound. All formula (III) compounds necessary as starting materials for making the formula (II) compounds are available commercially, for example, from Strem Chemicals Inc., Danvers, Mass.

The compounds of formula (I) wherein W is a per-O-acetyl thiosugar can be prepared by reacting the appropriate derivative of formula (II) with the appropriate per-O-acetyl- (thiopseudourea hydrobromide), all of which are available commercially or can be prepared by methods available to one skilled in the art. See, for example, Durette et al., *Carb. Res.*, 81, 261 (1980).

As an alternate route, the compounds of formula (I) wherein W is a non-acetylated thiosugar or selenosugar can be prepared from the corresponding per-O-acetyl derivative by treating the acetylated compound with a hydrolyzing base, such as methanolic ammonia or sodium methoxide in methanol, to give the desired non-acetylated compound of formula (I). The appropriate per-O-acetyl selenosugar starting material can be prepared by reacting the appropriate derivative of formula (II) with the appropriate per-O-acetyl-(selenopseudourea hydrobromide), all of which are available commercially or can be prepared by methods available to one skilled in the art. See, for example, Durette et al., *Carb. Res.*, 81, 261 (1980).

As stated above, the compounds of formula (I) have tumor cell growth-inhibiting activity which has been demonstrated in a variety of test systems.

The B16 mouse melanoma cell assay measures the ability of a compound to inhibit the clonogenic capacity of cells in vitro following a two hour exposure to the compound. The cytotoxic activity of the compounds of formula (I) was evaluated in vitro using B16 melanoma cells according to the following protocol:

B16 melanoma (highly metastatic subline, F10) are used and maintained as monolayer cultures in Minimal Essential Media (Grand Island Biological Co., Grand Island, N.Y.) supplemented with 10% calf serum, 1% antibiotics in a 5% $CO_2$ humidified incubator at 37° C. Asynchronous populations of cells are harvested and replated to 5000 cells/plate in sterile 60 mm×15 mm petri plates. Plates are incubated overnight to allow attachment of the cells to the plate. Cells are treated with the compound to be evaluated under sterile conditions, allowed to react for 2 hours followed by aspiration of medium. Plates are washed one time with 5 ml of phosphate buffered saline (PBS), followed by the addition of 5 ml of fresh media. Plates are incubated for 5 days at 37° in a $CO_2$ incubator. Viability is measured by the ability of a cell to form a colony of greater than 50 cells. Colonies are fixed with 0.5% crystal violet in 95% ethanol. Plates are dried and counted with a Biotran III Automatic Count Totalized (New Brunswick Scientific Co., Edison, N.J.). Mean and standard deviation of triplicate samples are determined for each drug concentration. The data are analyzed by plotting the log of the survival fraction (number of colonies in drug treated plates/number of colonies in controls) versus the drug concentration.

An evaluation of one particular compound of formula (I) in the in vitro B16 cytotoxic assay is shown in Table I.

TABLE I

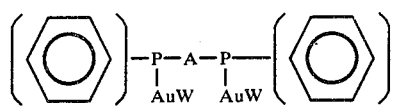

| Compound No. | A | W | $IC_{50}$ (+FCS)[a] ($\mu M$) |
|---|---|---|---|
| 1 | $(CH_2)$ | 1-thioglucose | 1 ± 0.2 |

[a]concentration of drug which inhibits cloning efficiency of B16 melanoma cells by 50% upon 2-hour exposure; drug exposure in the presence of 10% fetal calf serum.

Additionally, in another in vitro assay, Compound No. 1 effectively killed HT-29 human colon carcinoma cells, with an $IC_{50}$(+FCS) of 5 $\mu M$ following a 2 hour exposure.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of formula (I) is demonstrated in the P388 leukemia mouse model employing the following protocol:

$10^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of either N,N-dimethylacetamide (DMA) or 95% ethanol (depending upon solubility). An equal volume of saline is added; if the drug comes out of solution an equal volume of polyethoxylated castor oil is added and then saline qs to a concentration such that the desired dose is delivered in 0.5 ml. The final concentration of DMA, ethanol and polyethoxylated castor oil is 10 percent. Dilutions for lower doses are made with saline so there is a decreasing proportion of organic solvents in the vehicle with decreasing dosage. These vehicles provide soluble formulations (or suspensions). Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change ($\Delta$wt.) is used as a reflection of toxicity. Each experiment also includes an inoculum titration—groups of 8 mice inoculated ip with $10^5$ to $10^\circ$ P388 leukemia cells. The titration is used to calculate cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 10 or 11 days. A drug is considered active if it produces $\geq 25$ percent ILS.

A summary of the evaluation of several compounds of formula (I) in the in vivo P388 model is shown in the following Table A.

TABLE A $$\left(\left(\bigcirc\right)\right)_2 - \underset{\underset{AuW}{|}}{P} - A - \underset{\underset{AuW}{|}}{P} - \left(\left(\bigcirc\right)\right)_2 \quad (I)$$

| Compound Number | A | W | MTD[a] (μM/kg) | ILS (Max)[b] (%) |
|---|---|---|---|---|
| 1 | (CH$_2$)$_2$ | 1-thioglucose | 5 | 86 ± 8[d] |
| 2 | (CH$_2$)$_2$ | 1-thioglucose (OAC)$_4$[c] | 2.6 | 35/35/28/95 |
| 3 | (CH$_2$)$_2$ | 1-thiomannose- (OAC)$_4$ | 2.6 | 30/30/25 |
| 4 | (CH$_2$)$_2$ | 1-thiogalactose | 3.4 | 85/100/147 |
| 5 | (CH$_2$)$_2$ | 1-thiomannose | 5 | 90/74 |
| 6 | (CH$_2$)$_3$ | 1-thioglucose | 5 | 28/56/41 |
| 7 | (CH$_2$)$_2$ | 1-selenoglucose | 9.4 | 36/27 |
| 8 | (CH$_2$)$_2$ | 1-thioribofuranose | 6 | 50/56 |

[a]maximally tolerated dose for B6D2F female mice on an ip qD × 5 regimen.
[b]maximum increase in lifespan produced in mice bearing ip P388 leukemia (figures separated by slashes indicate data generated in separate experiments).
[c]1-thioglucose-(OAC)$_4$ = tetra-O—acetyl-1-thioglucose.
[d]number based on data from twelve separate experiments.

Based on the data set forth in Table A, compounds of formula (I) showed significant antitumor activity in the in vivo ip P388 leukemia tumor assay. In particular, Compounds No. 1, 2 and 3 have particularly good activity in the P388 leukemia assay with an ILS comparable to the clinically useful antitumor agent cisplatin.

Another chemosensitive tumor model is intraperitoneally (ip) implanted M5076 reticulum cell sarcoma in mice. In this system B6D2F female mice are inoculated with 0.5 ml of a 10 percent (w:v) brei of M5076 prepared from pooled subcutaneous (sc) tumors excised at about 21 days from C57B1/6 donors. Drugs are administered ip. Daily treatement is begun 24 hours after implantation and is continued for ten days. The treatment regimen for M5076 is more prolonged than for P388 because of the slower growth rate and longer control survival time of the M5076 tumor. The antitumor activity of Compounds No. 1 and No. 2 of Table A in the M5076 reticulum cell sarcoma tumor model is set forth in Table 2.

TABLE 2

| Compound No.[a] | ILS (MAX) (%)[b] | MTD (μM/kg)[c] |
|---|---|---|
| 1 | 109/38/45/65 | 3.4 |
| 2 | 67 | 2 |
| 4 | 37 | 3.5 |
| 6 | 35 | 3.5 |
| 7 | 46 | 3.1 |

[a]see Table A for structures.
[b]maximum increase in lifespan produced in mice bearing ip M5076 reticulum cell sarcoma (figures separated by slashes were generated in separate experiments).
[c]maximally tolerated dose for B6D2F female mice on an ip qD × 10 regimen.

The cytotoxic activity of Compound No. 1 from Table A was evaluated in vivo using B16 melanoma cells. In this system, groups of eight B6D2F$_1$ mice are inoculated ip with 0.5 ml of a 10% (w:v) brei of B16 melanoma prepared from pooled sc tumors excised at 14–21 days from C67B$_1$/6 donor mice. Daily treatment is begun 24 hours after tumor implantation and is continued daily for ten (10) days. The route of drug administration is ip. The mice are monitored daily for survival for sixty (60) days. Antitumor activity is assessed by prolongation of median survival time. An ILS of $\geq 25\%$ indicates activity in this tumor model.

A summary of the results of the in vivo ip B16 melanoma assay is shown in Table 3.

TABLE 3

| Compound No.[a] | MTD (μM/kg)[b] | ILS (%)[c] |
|---|---|---|
| 1 | 3.4 | 37/26 |

[a]see Table A for structure.
[b]maximally tolerated dose for B6D2F$_1$ mice on an ip of qD × 10 regimen.
[c]maximum increase in lifespan produced in mice bearing ip B16 melanoma (figures separated by a slash were generated in separate experiments).

Similarly, in another additional in vivo tumor model, namely B16 melanoma in mice, Compound No. 1 from Table A, administered ip in a dosage schedule of 8, 4, 2, 1 and 0.5 mg/kg produced an average increase in lifespan (ILS) of 32% at a maximally tolerated dose (MTD) of 3.4 μM/kg.

Compound No. 1 from Table A was also tested in a further in vivo tumor model, mammary adenocarcinoma 16/c, a tumor model sensitive to DNA binders and alkylating agents. In this experiment, the tumor was implanted sc in C3H mice, and the drug was administered ip or iv on an intermittant treatment schedule, i.e., once on days 1, 5, 9, 13 and 17. Tumors were measured 3 weeks after implantation, and activity was assessed by degree of tumor growth inhibition. Cisplatin, a drug which generally produces complete inhibition of the growth of mammary adenocarcinoma 16/c, was used as a positive control. A tumor growth inhibition of $\geq 75\%$ indicates that a drug is active in this type of animal tumor model. The results of this assay are summarized in Table B.

TABLE B

| Drug | Route and Schedule of Administration | Optimal Dose (mg/kg) | Mean Tumor Volume (mm$^3$) on Day 21 | Inhibition (%) | N.P.* |
|---|---|---|---|---|---|
| Experiment 1 | | | | | |
| Control | | | 1187 ± 999 | | 1/24 |
| Cisplatin | ip, q4D × 5 | 6 | 30 ± 64 | 97 | 6/8 |
| Compound No. 1 | ip, q4D × 5 | 12 | 42 ± 60 | 96 | 3/5 |
| Experiment 2 | | | | | |
| Control | | | 1113 ± 626 | | 0/23 |
| Cisplatin | ip, q4D × 5 | 6 | 0 | 100 | 8/8 |
| | ip, q4D × 5 | 6 | 21 ± 61 | 98 | 7/8 |
| | ip, q4D × 5 | 8 | 711 ± 268 | 36 | 0/7 |
| Compound No. 1 | iv, q4D × 5 | 16 | 243 ± 106 | 78 | 0/8 |

*N.P. = Proportion of mice without palable tumors on Day 21

Likewise, Compound No. 1 from Table A was tested in an additional in vivo tumor model known as ADJ-PC6 Plasmacytoma. In this assay, tumor cells are carried by serial sc passage in BALB/c female mice and then collected aseptically on ca. day 21 and minced in Hank's balanced salt solution. The cells are then dispersed by homogenization in a loose-fitting teflon glass homogenizer, and cell concentration is adjusted to $4 \times 10^6$ viable (trypsin blue-excluding) cells per ml by hemocytometer counts. A total of 0.5 ml ($2 \times 10^6$ cells) is implanted sc on the right flank of BALB/c female mice in groups of 8. Treatment is given ip on Days 1–10, and tumors are measured in perpendicular diameters with a vernier caliper on Day 18. Tumor volume is calculated by multiplying length×width²×0.5. Generally, ≧75% inhibition of tumor growth reflects significant antitumor effect. Cisplatin, the positive control compound, produces complete tumor growth inhibition. The results of this assay are summarized in Table C.

TABLE C

| Drug | Dose (mg/kg/day × 10, ip) | N.P.[a] | Tumor Growth Inhibition (Day 18) MTV[b] | % Inhibition |
|---|---|---|---|---|
| Compound No. 1 | 6 | 6/7 | 11 ± 28 | 98[c] |
| Compound No. 1 | 3 | 0/8 | 295 ± 163 | 50 |

[a]N.P. = Proportion of mice without palpable tumor on Day 18.
[b]MTV = Mean Tumor Volume (mm³) on Day 18.
[c]In another experiment at the same dose and same treatment schedule, Compound No. 1 gave only 23% inhibition of ADJ-PC6 Plasmacytoma.

The pharmaceutical compositions of this invention comprise an effective tumor cell growth-inhibiting amount of a compound of formula I and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hyroxypropyl cellulose or other suitable suspending agent. As an emulsifying agent, lecithin for example may be used. The composition may also be provided in the form of a sterile solid which can be dissolved in a sterile injectable medium immediately before use.

It will be appreciated that the actual preferred dosages of the compounds of formula I used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of formula (I) contacts the tumor. Optimal dosages for a given set of conditions can be ascertained by those skilled in the art using conventional dosage determination tests in view of the above experimental data. For parenteral administration the dose generally employed is from about 5 to about 20 mg/m² of body surface per day for one to five days, repeated about every fourth week for four courses of treatment.

The method for inhibiting the growth of animal tumor cells sensitive to a compound of formula (I) in accordance with this invention comprises administering to a host animal afflicted with said tumor cells, an effective tumor cell growth-inhibiting amount of a compound of formula I. As described above, during the course of treatment the active ingredient will be administered parenterally in an amount selected from about 300 mg to about 1000 mg.

EXAMPLES

The following examples illustrate the chemical preparation of several compounds of formula I which are used in the compositions and methods of this invention and as such are not to be construed as limiting the scope thereof. All temperatures are in degrees Centigrade.

EXAMPLE 1

μ-[1,2-Bis(Diphenylphosphino)Ethane]bis[1-Thio-β-D-Glucopyranosato-S)Gold(I)]

a. μ-[1,2-Bis(diphenylphosphino)ethane]bis[chlorogold(I)]

Thiodiglycol (11.0 g, 0.09 mol) in methanol (50 ml) was added dropwise over 15 minutes to a solution of chloroauric acid tetrahydrate (12.4 g, 0.03 mol) in water (100 ml)/methanol (150 ml) kept at 0°. After stirring an additional 15 minutes, 1,2-bis(diphenylphosphino)ethane (6.12 g, 0.015 mol), obtained from Strem Chemicals, Inc., Danvers, Mass., in chloroform (100 ml)/methanol (100 ml) was added to the colorless solution (immediate ppt upon addition). After warming to room temperature (2 hours), methanol (0.5 ) was added and the product collected, slurried with methylene chloride/ethanol, filtered and dried to give 11.0 g (85%) of white product which had a melting point of 290°-292°.

By using substantially the method described above and employing the appropriate ligand of formula (III), any other desired derivative of formula (II) can be obtained.

b. μ-[1,2-Bis(diphenylphosphino)ethane]bis[1-thio-β-D-glucopyranosato-S)gold(I)]

Under an argon atmosphere at ambient temperature, μ-[1,2-bis(diphenylphosphino)ethane]bis[chlorogold(I)] (5.0 g, 5.8 mmol), prepared as described in part A, in chloroform (500 ml)/ethanol (200 ml) was added to a rapidly stirred solution of sodium thioglucose (2.53 g, 11.6 mmol), obtained from Sigma Chemical Company, in water (100 ml)/ethanol (300 ml). After 72 hours of rapid stirring, the solvent was removed in vacuo. Chromatography (Waters Prep 500, silica gel) of the residue with 15% methanol/methylene chloride gave 3.57 g (52%) of solid which had a melting point of 130°; $[\alpha]^{25}_D$ (1% CH$_3$OH)−3.6°.

EXAMPLE 2

μ-1,2-Bis(Diphenylphosphino)Ethane]Bis[(1-Thio-β-D-Galactopyranosato-S)Gold(I)]

Under an argon atmosphere at ambient temperature, a mixture of sodium thiogalactose (1.25 g, 5.4 mmol), obtained from Sigma Chemical Company, and β-[1,2-bis(diphenylphosphino)ethane]bis[chlorogold(I)] (2.34 g, 2.72 mmol), prepared as described in Example 1, in ethanol (150 ml)/water (20 ml)/chloroform (200 ml) was stirred for 18 hours. The solvent was removed in vacuo, and the residue subjected to preparative high pressure liquid chromatography (HPLC) (Waters Prep 500, silica gel, 20% methanol/methylene chloride) to give 0.64 g of oily product. Treatment with acetone followed by recrystallization from methanol/ether gave 0.4 g (13%) of amorphous solid product; $[\alpha]_D^{25}$ (1% methanol)+3.9°.

EXAMPLE 3 μ-8
1,2-Bis(Diphenylphosphino)Ethane]Bis[(2,3,4,6-Tetra-O-Acetyl-1-Thio-α-D-Mannopyranosato-S)Gold(I)]

Under an argon atmosphere at 0°, potassium carbonate (0.42 g, 3.1 mmol) in water (10 ml) was added to a solution 2-S(2,3,4,6-tetra-O-acetyl-α-D-mannopyranosyl)-2-thiopseudourea hydrobromide (1.35 g, 2.77 mmol), prepared by the method of Durette et al., Carb. Res., 81, 261 (1980), in water (15 ml). After 15 minutes, ethanol (75 ml) was added and stirred 10 minutes followed by the addition of μ-[1,2-bis(diphenylphosphino)ethane]bis[chlorogold(I)] (1.08 g, 1.25 mmol), prepared as described in Example 1, in chloroform (100 ml). After stirring overnight, water (150 ml) was added, the layers separated, the organic layer dried (MgSO4), filtered and the chloroform removed in vacuo. Recrystallization of the residue from ethanol gave 0.87 g (46%) of white amorphorus solid; $[\alpha]_D^{25}$ (1% CH3OH)+52.1°.

EXAMPLE 4
μ-[1,2-Bis(diphenylphosphino)ethane]bis[1,thio-α-D-mannopyranosato-S)gold(I)]

A mixture of μ-[1,2-bis(diphenylphosphino)ethane]bis[2,3,4,6-tetra-O-acetyl-1-thio- -D-mannopyranosato-S)-gold] (1.0 g, 2.1 mmol), prepared as described in Example 3, and concentrated ammonium hydroxide solution (15 ml) in methanol (100 ml) was stirred at ambient temperature for 18 hours and the solvent evaporated in vacuo. Water and methanol were added and the mixture acidified to pH 4 with glacial acetic acid. The solvent was evaporated in vacuo and the residue washed with water. Chromatography of the residue (silica gel, 30% methanol/methylene chloride) gave an oily product which formed a white solid on treatment with acetone, and yielded 0.38 g (49%) of solid amorphous product; $[\alpha]_D^{25}$ (1% CH3OH)+52.2°.

EXAMPLE 5
μ-[1,2-Bis(diphenylphosphino)ethane]bis[2,3,4,6-tetra-O-acetyl-1-thio-β-D-glucopyranosato-S)gold(I)]

Under an argon atmosphere at ambient temperature, μ-[1,2-bis(diphenylphosphino)ethane]bis[chlorogold(I)] (1.0 g, 1.16 mmol), prepared as described in Example 1, in chloroform (100 ml) was added dropwise to a solution of potassium carbonate (0.32 g, 2.32 mmol) and 1-β-D-thio-2,3,4,6-tetra-O-acetylglucopyranose (0.84 g, 2.32 mmol), obtained from Aldrich Chemical Company, in water (40 ml)/ethanol (150 ml) followed by additional chloroform (50 ml)/ethanol (50 ml). After stirring for one hour, the solvent was evaporated in vacuo and the residue dissolved in chloroform, washed with water (twice), the organic layer dried (MgSO4), filtered and the solvent removed in vacuo. Chromatography (Waters Prep 500, silica gel) of the residue with 20% ethyl acetate chloroform gave 1.6 g (91%) of product as a white amorphous solid; $[\alpha]_D^{25}$ (1% CH3OH) −67.6°.

EXAMPLE 6
μ-[1,3-Bis(diphenylphosphino)propane]bis[1-thio-β-D-glucopyranosato-S)gold(I)]

Under an argon atmosphere at ambient temperature, a suspension of μ-[1,3-bis(diphenylphosphino)propane]-bis[chlorogold(I)] (0.55 g, 0.64 mmol), prepared as described in Example 1, in chloroform (75 ml) was added to a rapidly stirred solution of sodium thioglucose (0.3 g, 1.4 mmol), obtained from Sigma Chemical Company, in methanol (75 ml)/water (10 ml). After one hour, the solvent was removed in vacuo and the residue washed with water and decanted, methanol was added, the precipitate (NaCl) was collected from the ether/methanol solution, and ether added to the solution. After standing overnight the product was collected from the ether/methanol solution, washed with ether and dried to give 0.68 g (90%) of white solid which had a melting point of 125°.

EXAMPLE 7
μ-[1,2-Bis(diphenylphosphino)ethane]-bis[1-seleno-β-D-glucopyranosato-se)gold(I)]

a. μ-[1,2-Bis(diphenylphosphino)ethane]-bis[2,3,4,6-tetra-O-acetyl-1-seleno-β-D-glucopyranosato-se)gold(I)]

A solution of 0.69 g (5.0 mmol) of potassium carbonate in 3 ml of distilled water was stirred into an ice-cooled solution of 2.78 g (5.2 mmol) of 2-S (2,3,4,6-tetra-O-acetyl-β-D-glucopyranosyl(2-selenoisourea hydrobromide, prepared by the method of Wagner et al., Archiv. der Pharmazie, 297, 461 (1964), in 100 ml of water/methanol (1:1). The resulting suspension was stirred with 2.16 g (2.5 mmol) of μ-[1,2-bis(diphenylphosphino) ethane]bis[chlorogold(I)], prepared as described in Example 1, in 150 ml of chloroform. After one hour the chloroform layer was separated, concentrated in vacuo and the residue flash chromatographed on silica (EtOAc/CHCl3 1:1) to give 1.4 g of a white amorphous solid which had a melting point of 110°-118°.

b. μ-[1,2-Bis(diphenylphosphino)ethane-bis1-seleno-β-D-glucopyranosato-Se)gold(I)]

A mixture of 710 mg (0.44 mmol) of μ-[1,2-bis(diphenylphosphino)ethane]bis[2,3,4,6-tetra-O-acetyl-1-seleno-β-D-glucopyranosato-Se)gold(I)], prepared as described in part a, and 50 mg (0.92 mmol) of sodium methoxide in absolute methanol was stirred at room temperature until exchange of carbohydrate acetate with solvent was complete. Afterwards the mixture was cooled as excess sodium methoxide was neutralized by the addition of 0.053 ml of glacial acetic acid. The colorless solution was concentrated under reduced pressure. The solid residue was washed repeatedly with distilled water, collected and dried in vacuo to give 390 mg of pale yellow material which had a melting point of 130°-135°.

EXAMPLE 8
μ-[1,2-Bis(Diphenylphosphino)Ethane]-Bis[(2,3,5-Tri-O-Acetyl)(1-Thio-D-Ribofuranosato-S)Gold (I)]

a. 2,3,5-Tri-O-acetyl-D-ribofuranosylisothiouronium Bromide

Trimethylsilyl bromide, 4.9 g (0.032 mmol), was added dropwise to a stirred solution (0°-5°) containing 5.0 g (0.016 mol) of β-D-ribofuranose tetraacetate (Aldrich Chemical Company) in 30 ml of dry CH2Cl2 under argon. After the addition was completed, the mixture was allowed to warm and was maintained at room temperature (24 hrs) until conversion of the tetraacetate to triacetyl ribofuranosyl bromide was complete as indicated by $^1$H NMR [J. W. Gillard, Tet. Letters, 22, 513 (1981)]. Thereafter, the reaction mixture was concentrated under reduced pressure to a thick oil, and the oil was reconcentrated twice after redissolution in CH$_2$Cl$_2$ to remove residual trimethylsilyl bromide. The residue was finally redissolved in 30 ml of acetone, treated with 1.22g (0.016 mol) of thiourea, and stirred at reflux temperature for ½ hr. Then the mixture was cooled, and the solid was removed by filtration. Then the solid was washed with cold acetone and dried in vacuo to give 2.7 g of product which had a melting point of 128°-130°. The product was a mixture of α,β-anomers as indicated by $^1$H NMR (Gillard, cited above).

b. μ-[1,2-Bis(diphenylphosphino)ethane]-bis [(2,3,5-tri-O-acetyl)(1-thio-D-ribofuranosato-S)gold(I)]

A solution of 0.76 g (5.5 mmol) of potassium carbonate in 3 ml of distilled water was stirred into a cooled solution containing 2.16 g (5.2 mmol) of 2,3,5-tri-O-acetyl-D-ribofuranosylisothiouronium bromide, prepared as described above, in 100 ml of H$_2$O/MeOH (1:1). After the mixture had stirred in the cold for ½hr, 2.16 g (2.5 mmol)) of μ-[1,2-bis(diphenylphosphino)ethane]-bis [chlorogold(I)], prepared as described in Example 1, dissolved in 150 ml of CHCl$_3$, was rapidly added dropwise. The mixture was then stirred an additional 2½ hrs, and the CHCl$_3$ layer was separated and concentrated under reduced pressure to a thick syrup. The syrup was fractionated on silica gel (Baker Flash-Chrom) (25% MeOH/EtoAc) to give 1.97 g of product which was a mixture of α,β-anomers with the α-anomer predominating as indicated by $^1$H NMR [J. W. Gillard, Tet. Letters, 22, 513 (1981)].

EXAMPLE 9

μ-[1,2-Bis(Diphenylphosphino)Ethane]-bis [1-Thio-D-Ribofuranosato-S)Gold(I)]

A mixture of 1 g (0.74 mmol) of μ-[1, 2-bis(diphenylphosphino)-ethane]-bis[(2,3,5-tri-O-acetyl) (1-thio-α,β-D-ribofuranosato-S)gold(I)], prepared as described in Example 8, and 40 mg (0.74 mmol) of NaOMe in 50 ml of absolute MeOH was stirred under dry argon at room temperature for twenty minutes. It was then stirred with ion exchange resin (Biorad AG 50WX8, sulfonic acid form) until free of excess NaOMe. The resin was removed by filtration, and the filtrate was concentrated in vacuo. The oily residue was solidified by stirring water to give 480 mg of a white powder which had a melting point of 122°-128°.

What is claimed:

1. A [bis(diphenylphosphino)alkyl]bis-gold[I] compound of the formula

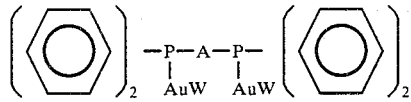

wherein:
A is (CH$_2$)n, or cis CH=CH;
n is 1 to 6; and
W is the same and is thiosugar or selenosugar.

2. The compound of claim 1 wherein W is 1-thioglucose, 1-thiogalactose, 1-thiomannose, 1-thioribose, 1-thiomaltose, 1-thiofucose, tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose, tri-O-acetyl-1-thiofucose, 1-selenoglucose, 1-selenomannose, 1-selenogalactose, 1-selenoribose, 1-selenomaltose, 1-selenofucose.

3. The compound of claim 2 wherein W is 1-thioglucose, 1-thiogalactose or 1-thiomannose.

4. The compound of claim 3 wherein W is (CH$_2$)$_2$ and W is 1-thioglucose.

5. A pharmaceutical composition which comprises an effective tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of the formula:

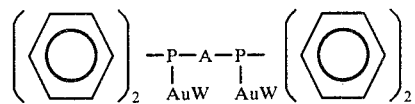

wherein:
A is (CH$_2$)n or cis CH=CH;
n is 1 to 6; and
W is the same and is thiosugar or selenosugar.

6. The composition of claim 5 wherein W is 1-thioglucose, 1-thiogalactose 1-thiomannose; 1-thioribose, 1-thiomaltose, 1-thiofucose, 1-thioribofuranose, tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose, tri-O-acetyl-1-thiofucose, 1-selenoglucose, 1-selenomannose, 1-selenogalactose, 1-selenoribose, 1-selenomaltose or 1-selenofucose.

7. The composition of claim 6 wherein W is 1-thioglucose, 1-thiogalactose or 1-thiomannose.

8. The composition of claim 7 wherein W is 1-thioglucose and A is (CH$_2$)$_2$.

9. The composition of claim 5 wherein the composition is in dosage unit form adapted for parenteral administration.

10. The composition of claim 9 wherein the parenteral dosage unit is adapted to administer from about 5 to about 20 mg/m$^2$ of body surface.

11. A method of inhibiting the growth of animal tumor cells sensitive to a compound of the formula:

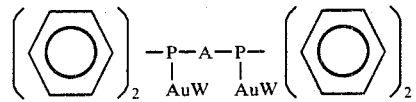

wherein:
A is (CH$_2$)$_n$ or cis CH=CH;
n is 1 to 6; and
W is the same and is thiosugar or selenosugar, which comprises administering to an animal afflicted with said tumor cells, an effective, tumor cell growth-inhibiting amount of said compound.

12. The method according to claim 11 wherein W is 1-thioglucose, 1-thiogalactose, 1-thiomannose, 1-thioribose, 1-thiomaltose, 1-thiofucose, 1-thiorifofuranose tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose, tri-O-acetyl-1-thiofucose, 1-selenoglucose, 1-selenomannose, 1-selenogalactose, 1-selenoribose, 1-selenomaltose or 1-selenofucose.

13. The method according to claim 12 wherein W is 1-thioglucose, 1-thiogalactose or 1-thiomannose.

14. The method according to claim 13 wherein W is 1-thioglucose and A is $(CH_2)_2$.

15. The method according to claim 11 wherein the administration is parenteral and the amount is selected from a unit dose range of from about 5 to about 20 mg/m$^2$ of body surface administered per dose for one to five days.

16. The method according to claim 15 wherein the administration is repeated about every fourth week for four courses of treatment.

17. The method according to claim 16 wherein during the course of treatment the amount administered is selected from about 300 to about 1000 mg.

* * * * *

UNITED STATES PATENT AND TRADEMARK OFFICE
CERTIFICATE OF CORRECTION

PATENT NO. : 4,645,756
DATED : February 24, 1987
INVENTOR(S) : David T. Hill and Randall K. Johnson It is certified that error appears in the above-identified patent and that said Letters Patent is hereby corrected as shown below:

On the title page Insert

-- (63) Related U.S. Application Data
Continuation-in-part of Serial No. 693,416 filed January 22, 1985, abandoned. --

Claim 2 at Column 11, line 65, insert the word

-- 1 - thioribofuranose -- after "1 - thiofucose"

Claim 4 at Column 12, line 5, delete "W" and insert -- A -- therefor

Claim 12 at Column 12, line 62, delete "1-thiorifofuranose" and insert -- 1-thioribofuranose -- therefor Signed and Sealed this Eighth Day of December, 1987

Attest:

DONALD J. QUIGG

Attesting Officer

Commissioner of Patents and Trademarks